US008905968B2

(12) United States Patent
Thomas (10) Patent No.: US 8,905,968 B2
(45) Date of Patent: Dec. 9, 2014

(54) SYSTEM FOR COOLING AND PRESSURIZING FLUID

(75) Inventor: Jeffrey E. Thomas, Hillsborough, CA (US)

(73) Assignee: Encephalon Technologies, LLC, San Francisco, CA (US)

( * ) Notice: Subject to any disclaimer, the term of this patent is extended or adjusted under 35 U.S.C. 154(b) by 58 days.

(21) Appl. No.: 13/186,253

(22) Filed: Jul. 19, 2011

(65) Prior Publication Data

US 2012/0191069 A1    Jul. 26, 2012

Related U.S. Application Data

(63) Continuation-in-part of application No. 12/431,889, filed on Apr. 29, 2009, now abandoned.

(51) Int. Cl.
*A61F 7/12* (2006.01)
*A61M 27/00* (2006.01)
*A61F 7/00* (2006.01)

(52) U.S. Cl.
CPC ............... *A61F 7/12* (2013.01); *A61M 27/006* (2013.01); *A61F 2007/0063* (2013.01); *A61F 2007/0086* (2013.01); *A61F 2007/126* (2013.01)
USPC ................................ 604/113; 604/27; 604/43

(58) Field of Classification Search
USPC ................................ 604/27, 43, 113; 607/105
See application file for complete search history.

(56) References Cited

U.S. PATENT DOCUMENTS

| | | |
|---|---|---|
| 3,504,674 A | 4/1970 | Swenson et al. |
| 4,666,426 A | 5/1987 | Aigner |
| 4,686,085 A | 8/1987 | Osterholm |
| 4,781,672 A | 11/1988 | Hooven |
| 4,795,423 A | 1/1989 | Osterholm |
| 4,840,620 A | 6/1989 | Kobayashi et al. |
| 4,856,972 A | 8/1989 | Van Benschoten et al. |
| 4,904,237 A | 2/1990 | Janese |
| 5,061,241 A | 10/1991 | Stephens, Jr. et al. |
| 5,085,630 A | 2/1992 | Osterholm et al. |
| 5,409,547 A | 4/1995 | Watanabe et al. |
| 5,423,807 A | 6/1995 | Milder |
| 5,529,067 A | 6/1996 | Larsen et al. |
| 5,597,377 A | 1/1997 | Aldea |
| 5,792,094 A | 8/1998 | Stevens et al. |
| 5,895,964 A | 4/1999 | Nakayama |
| 5,950,067 A | 9/1999 | Maegawa et al. |
| 5,954,665 A | 9/1999 | Ben-Haim |
| 6,042,559 A | 3/2000 | Dobak, III |
| 6,051,019 A | 4/2000 | Dobak, III |
| 6,161,388 A | 12/2000 | Ghoshal |
| 6,217,552 B1 | 4/2001 | Barbut et al. |
| 6,623,514 B1 | 9/2003 | Chin |
| 6,896,663 B2 | 5/2005 | Barbut |

(Continued)

*Primary Examiner* — Emily Schmidt
(74) *Attorney, Agent, or Firm* — Benesch Friedlander Coplan & Aronoff LLP (57) ABSTRACT

A pump for delivering a fluid, created by cooling and pressurizing a fluid, into the intrathecal space of a patient, the pump comprising an input channel, an input reservoir in fluid communication with the input channel, a cooling apparatus configured to remove heat from the fluid and a pressurizing mechanism configured to impart pressure to the fluid, an output reservoir, and an output channel, and wherein the output channel is configured to be in fluid communication with a first lumen of a catheter and wherein the first lumen of the catheter is configured to be disposed within the intrathecal space of the patient.

16 Claims, 6 Drawing Sheets

(56) References Cited

U.S. PATENT DOCUMENTS

| | | |
|---|---|---|
| 6,942,633 B2 | 9/2005 | Odland |
| 7,004,961 B2 | 2/2006 | Wong |
| 7,318,834 B2 | 1/2008 | Njemanze |
| 7,455,666 B2 | 11/2008 | Purdy |
| 7,842,002 B2 | 11/2010 | Mantle |
| 2004/0243058 A1* | 12/2004 | Barbut et al. ............... 604/113 |
| 2006/0161107 A1* | 7/2006 | Mantle ........................ 604/113 |
| 2010/0022896 A1* | 1/2010 | Yadav et al. ............... 600/488 |

* cited by examiner

FIG. 5

SYSTEM FOR COOLING AND PRESSURIZING FLUID

RELATED APPLICATIONS

This application claims priority to U.S. patent application Ser. No. 12/431.889. filed on Apr. 29, 2009. entitled Bidirectional Cerebral Spinal Fluid Infusion Catheter with Cooling Mechanism and Method of Use.

FIELD OF THE INVENTION

This application relates in general to a system and method for reliably selectively cooling the tissue of the central nervous system (CNS) that does not require systemic cooling of the body. Specifically, the method includes the use of a dual lumen catheter that imparts localized, targeted cooling of the CNS tissue by cooling the cerebrospinal fluid (CSF) surrounding said nervous tissue.

BACKGROUND

Hypothermia is well established as a neuroprotective strategy for brain injury (stroke, trauma, malignant edema). Currently hypothermia is administered systemically. This intervention is associated with significant medical complications, among them bleeding, pulmonary infection, and the need for sedation with mechanical ventilation, and, often, pharmacologic paralysis.

No effective treatment for damage to the CNS, such as completed infarction, hemorrhage, or trauma exists. This is particularly true for damage to the spinal cord, which renders a human immobile and for which there is no specific remedy.

SUMMARY

A system for treating or preventing damage to a patient's central nervous system and a method for using the same include a catheter comprising at least a first lumen and a second lumen, wherein the first lumen includes a proximal end having at least one inflow portal and a distal end having at least one outflow portal, and the second lumen including a proximal end and a distal end and a sidewall extending between the proximal end and the distal end. The sidewall of the second lumen includes at least one side portal providing fluid communication between an outer surface of the sidewall and an inner surface of the sidewall. The proximal end of the second lumen also includes at least one outflow portal.

The system also includes a pump with at least one input channel, an input reservoir in fluid communication with said at least one input channel, a cooling apparatus configured to remove heat from a fluid, a pressurizing mechanism configured to impart pressure to the fluid, an output reservoir, and an output channel. The pump is configured to pressurize and cool a fluid and deliver the fluid to the body of the patient.

In one embodiment, the first lumen of the catheter is substantially concentrically disposed within the second lumen of the catheter and in yet another embodiment, the first lumen is longitudinally adjacent the second lumen and the lumen are separated by a partitioning wall.

In one embodiment, the output channel is configured to be connected to the inflow portal of the first lumen and the outflow portal of the second lumen is configured to be connected to the input channel of the input reservoir, a waste container, or both. In the embodiment where the outflow portal of the second lumen is connected to the waste container. the input channel of the input reservoir is configured to be in fluid communication with a third reservoir.

DESCRIPTION OF THE DRAWINGS

In the accompanying drawings, structures are illustrated that, together with the detailed description provided below, describe exemplary embodiments of the claimed invention.

In the drawings and description that follows, like elements are identified with the same reference numerals. The drawings are not to scale, and the proportion of certain elements may be exaggerated for the purpose of illustration.

DETAILED DESCRIPTION

Figure 1:
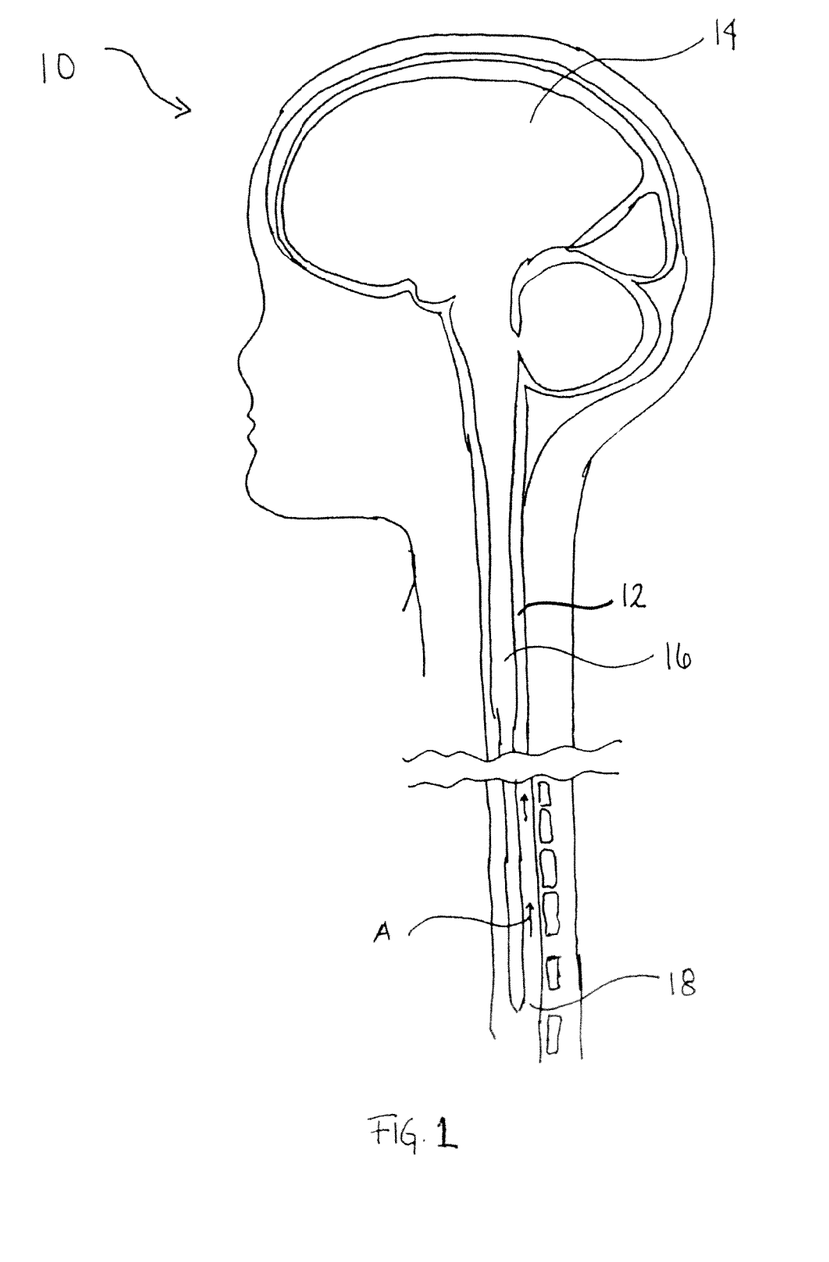
FIG. 1 is across sectional view of the central nervous system, including the brain and spinal cord.

Naturally-occurring CSF is a clear liquid that occupies the intrathecal space 12 in the patient's CNS 10, the space between the arachnoid mater (the middle layer of meninges) and the pia mater (the layer of the meninges closest to the brain 14). As shown in FIG. 1, unlike blood, CSF in the intrathecal space 12 directly contacts and circulates around the tissue of the brain 14, the spinal cord 16, and the blood vessels surrounding the brain 14 (not shown). CSF is an ideal carrier for neuroprotective agents and other such neurological treatments that may be helpful for patients who have recently undergone a stroke, potential cerebral or spinal ischemia, trauma to the spinal cord 16 or brain 14, subarachnoid hemorrhage, intracerebral hemorrhage, brain tumor, or any condition where CNS damage, cerebral swelling or spinal cord swelling is manifest or expected.

Figure 4:
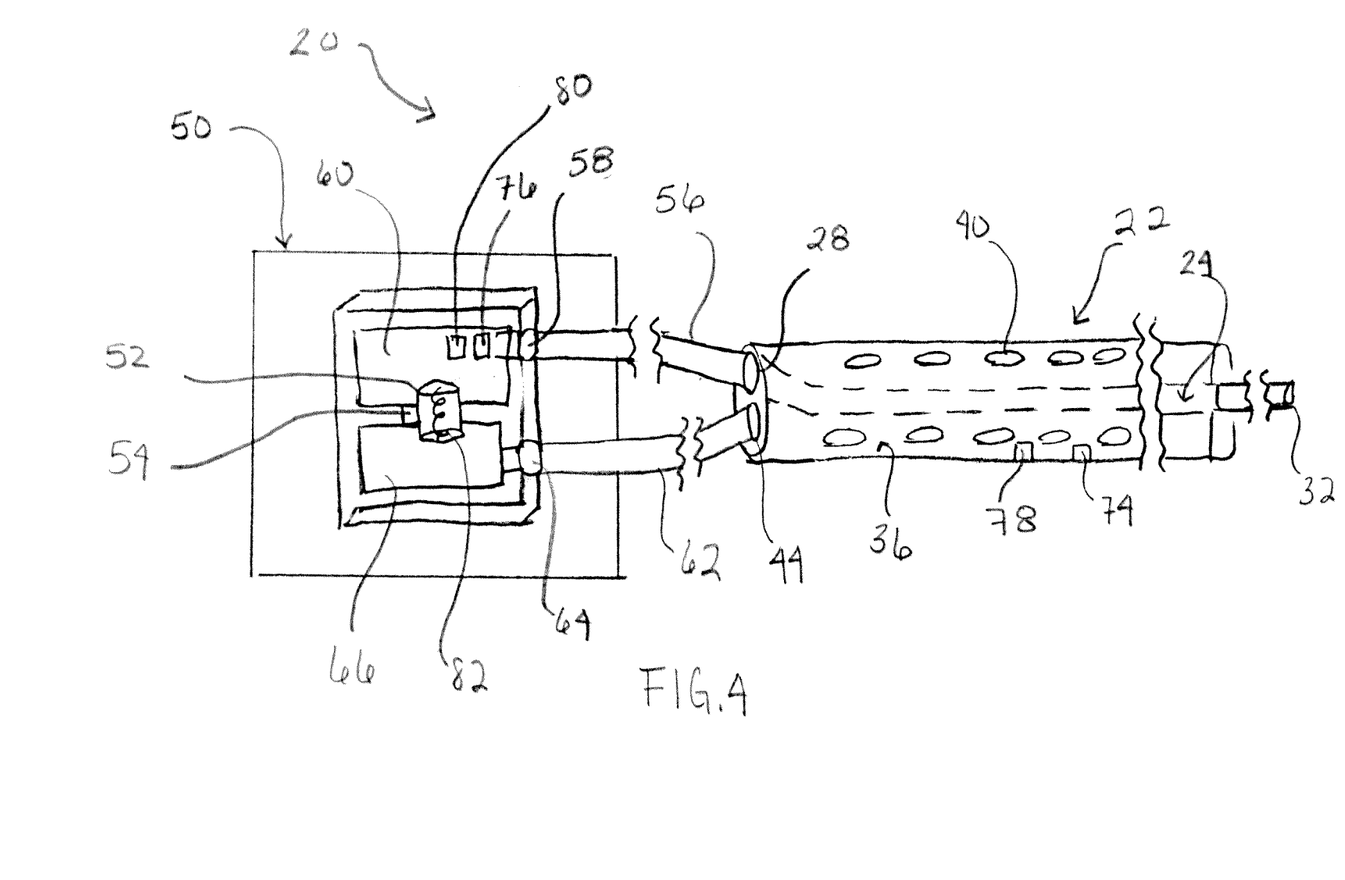
FIG. 4 is a cross sectional view of an embodiment of a system including a dual lumen catheter of FIG. 2 with a pump.
Figure 5:
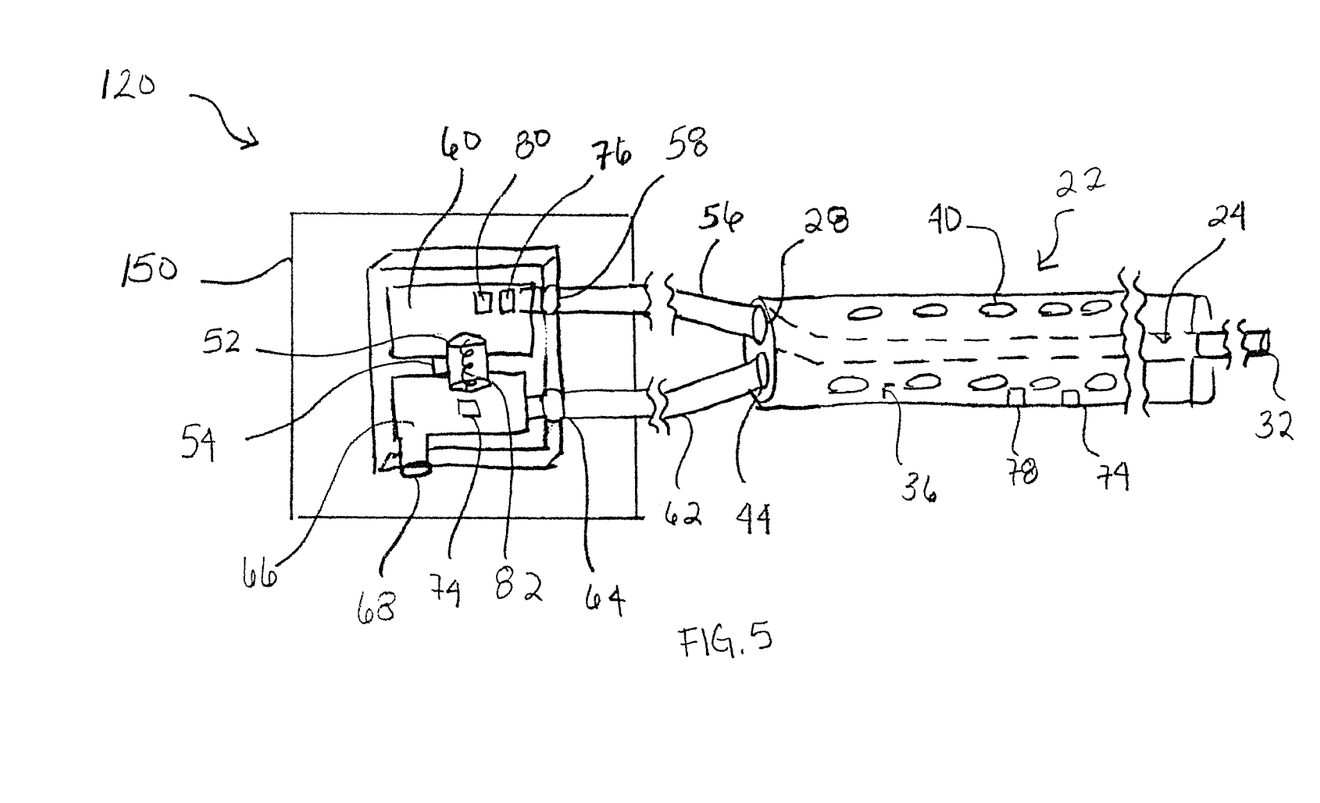
FIG. 5 is a cross sectional view of another embodiment of a system including a dual lumen catheter of FIG. 2 with a pump.
Figure 6:
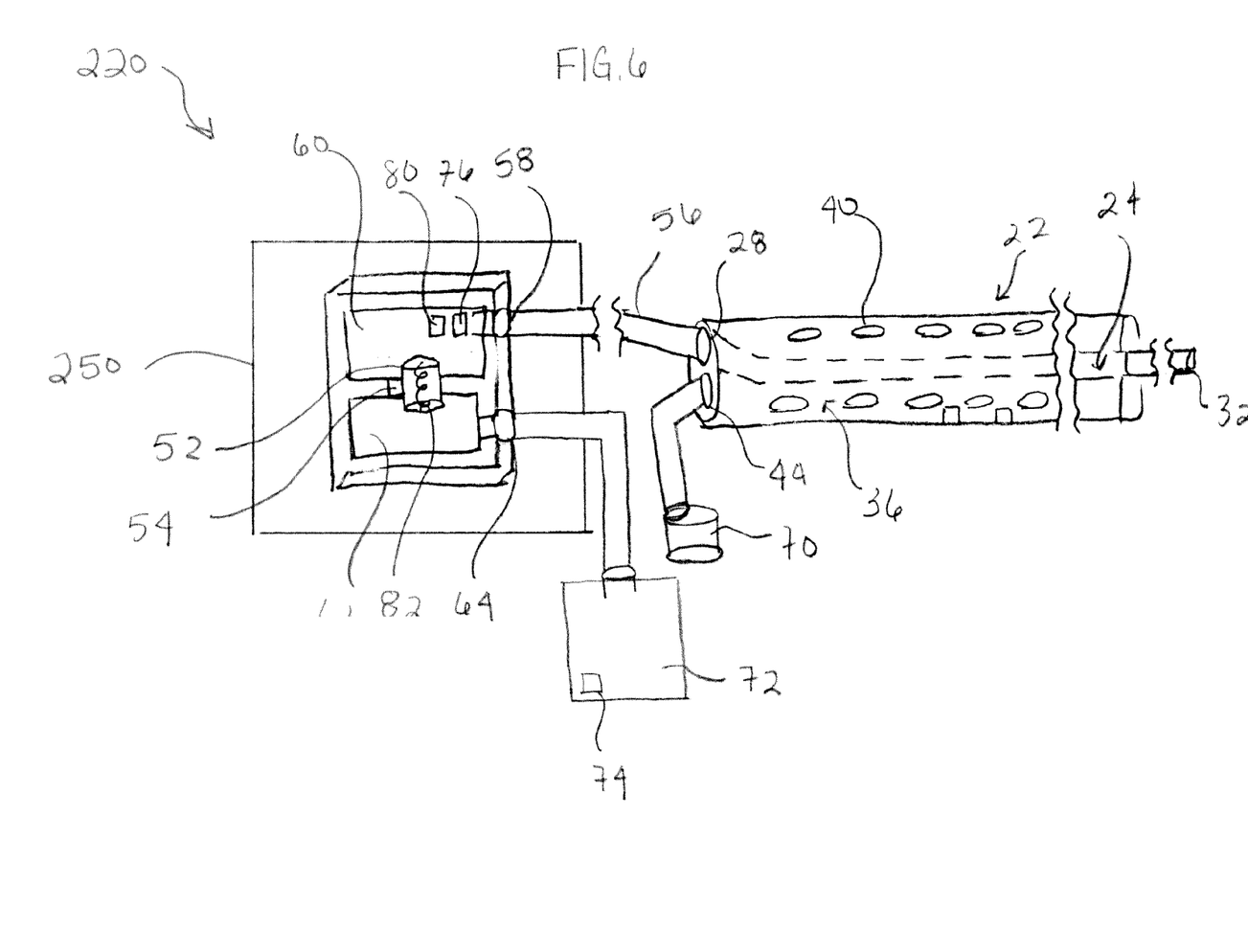
FIG. 6 is a cross sectional view of yet another embodiment of a system including a dual lumen catheter of FIG. 2 with a pump.

In one embodiment, a system 20 is provided that includes a catheter 22 and a pump 50 (FIGS. 4-6). The system 20 enables a physician to provide a patient with a cooled and/or pressurized fluid from the pump 50, through the catheter 22, and into the intrathecal space 12 surrounding the patient's spinal cord 16 and brain 14. Generally, the fluid is both cooled and pressurized by the pump 50.

Referring again to FIG. 1, a fluid can be administered to a patient's intrathecal space 12 using the catheter 22 (shown in FIGS. 2-6) to infuse the fluid into the patient. The fluid can then travel throughout the CNS 10, such as by the route indicated by arrow A, and circulate around the spinal cord 16 and brain 14. The patient's intrathecal space 12 is often accessed below the L1 lumbar vertebrae level, through a lumbar access point 18, to minimize the risk of direct damage to the spinal cord 16 by the introducer needle. It should be recognized, however, that the fluid may be administered to the space surrounding the brain 14 or spinal cord 16 using any known method of accessing the CSF of a patient including, but not limited to, ventriculostomy, or by needle access to the cisterna magna.

When a cooled fluid is delivered to the patient, the patient's CNS is cooled by convection or fluid-fluid heat transfer. This type of system may be used to prevent tissue ischemia and stroke, as chemotherapy for CNS malignancy, and to transport antibiotics for CNS infection. Moreover, it is contemplated that such a system may be used for therapeutic irrigation of CSF, as for example in severe leptomeningeal infection or subarachnoid hemorrhage.

Figure 2:
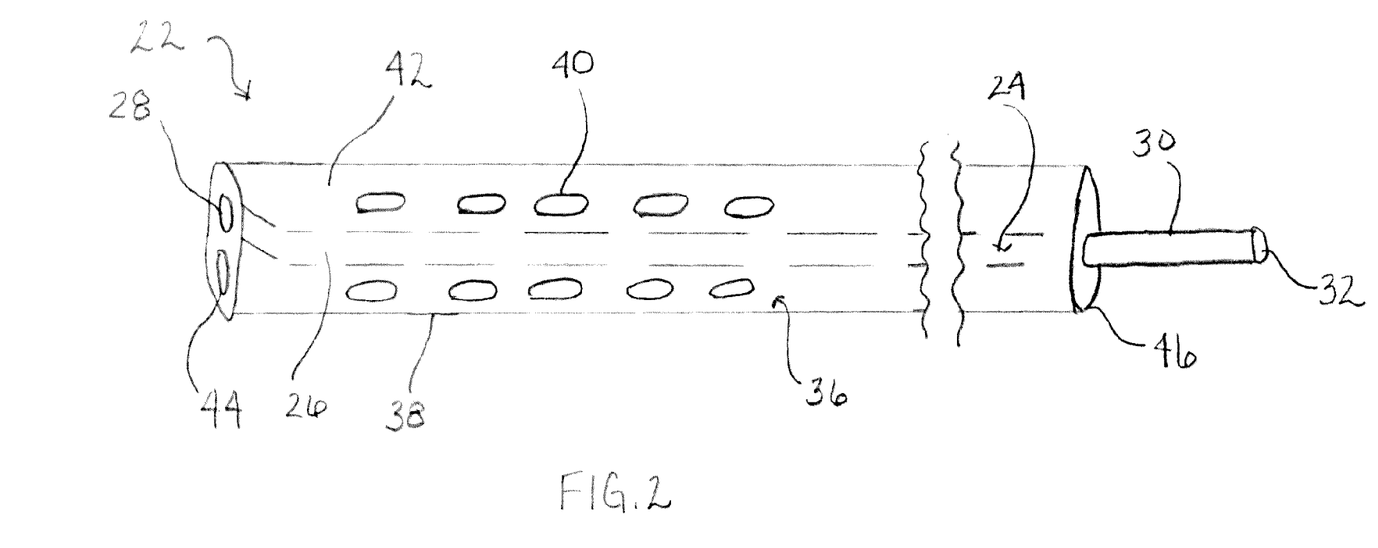
FIG. 2 is a side view of a dual lumen catheter.

Referring to FIG. 2, in one embodiment, the catheter 22 is generally an elongate tubular member and includes at least a first lumen 24 and a second lumen 36. As shown in FIG. 2, the catheter 22 may be comprised of two separate catheters, one inside the other, providing a first lumen 24 and second lumen 36. The first lumen 24 includes a proximal end 26 with an inflow portal 28 and a distal end 30 having an outflow portal 32. The outflow portal 32 of the first lumen 24 is designed to facilitate the flow of a fluid from the system 20 into the patient's intrathecal space 12.

The second lumen 36 includes a sidewall 38 with at least one side portal 40 providing fluid communication between the second lumen 36 and the exterior of the catheter 22. The second lumen 36 also includes a proximal end 42 and an outflow portal 44. Notably, the distal end 46 of the second lumen 36 is closed to fluid communication with the exterior of the catheter 22. As shown in FIG. 2, the second lumen 36 may have a plurality of side portals 40 along the sidewall 38. The portion of the sidewall 38 having side portals 40 may extend the length of the sidewall 38 of the second lumen 36 or may cover only a portion of the sidewall 38. The side portals 40 are designed to facilitate the egress of the patient's un-cooled, un-pressurized, naturally occurring CSF (native CSF) from the patient's body into the system 20.

Increasing the number and placement of the side portals 40 may be advantageous to the egress of native CSF from the patient's intrathecal space. Moreover, increasing the number of side portals 40 reduces the likelihood that the side portals 40 will be blocked by the free-floating spinal nerve roots that exist in the intrathecal space.

In this embodiment, the first lumen 24 of the catheter 22 is substantially concentrically disposed within the second lumen 36. Moreover, the distal end 30 of the first lumen 24 of the catheter 22 extends beyond the distal end 46 of the second lumen 36. In this embodiment, the location of the outflow portal 32 of the first lumen 24, relative to the side portals 40 of the second lumen 36, facilitates the dispersion of fluid exiting the outflow portal 32 of the first lumen 24 throughout the intrathecal space and around the patient's brain. This distance also affects the specific flow dynamic between the native CSF flowing into the second lumen 36 of the catheter 22 through the side portals 40 and the fluid being dispersed from the outflow portal 32 in the first lumen 24. The distance can be varied depending on the intended target of the fluid and the amount of pressure applied to the fluid from the pump (discussed below).

The side portals 40 are desirably placed a sufficient distance away, along the horizontal axis, from the outflow portal 32 of the first lumen 24. The distance between the side portals 40 and the outflow portal 32 of the first lumen 24 will prevent the fluid that is discharged from the first lumen 24 from being immediately recirculated into the second lumen 36.

In one embodiment, the catheter 22 is about 170 mm to about 210 mm in length and from about 1 mm to about 4 mm in diameter, although any catheter of a size and shape that can be inserted into the intrathecal space of a patient without causing damage to the surrounding tissue is contemplated. In one embodiment, the catheter 22 is introduced into the lumbar access point of the patient with a 14 gauge tuohy needle (not shown), and thus the catheter 22 must fit within the needle. In another embodiment, it is contemplated that the catheter 22 is introduced into the lumbar access point through about a 14 gauge plastic sleeve (not shown) that may remain within the patient until administration of the fluid is complete.

The catheter 22 may be composed of any suitable polymeric or metallic material, such as polyethylene, titanium, nitinol, or stainless steel. The catheter 22 may also include a tip (not shown) for easily inserting the catheter 22 into the patient's intrathecal space.

Figure 3:
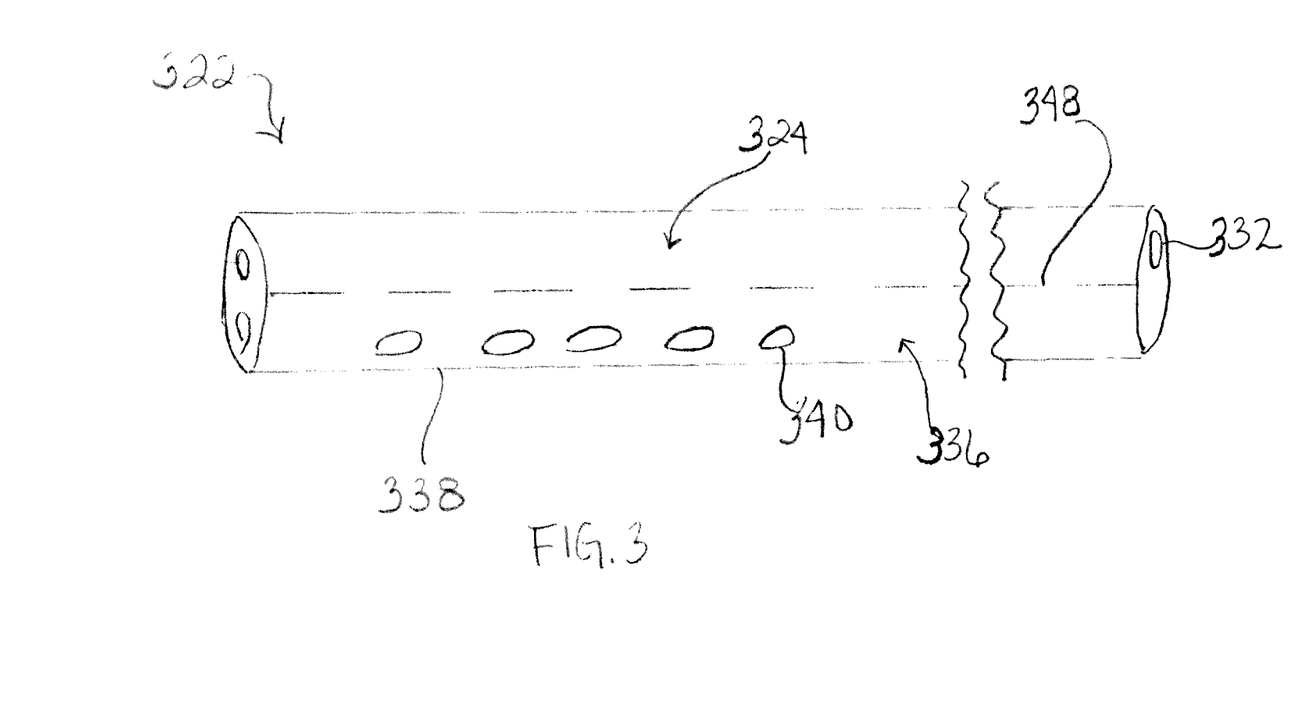
FIG. 3 is a side view of another embodiment of a dual lumen catheter.

In another embodiment, as shown in FIG. 3, rather than being concentrically located within the second lumen 336, the catheter 322 may be divided into a first lumen 324 and a second lumen 336 with a partitioning wall 348. In this embodiment, the first lumen 324 and second lumen 336 are semi-circular in cross-section and are positioned side-by-side. The first lumen 324 and second lumen 336 may have similar or varied radii. Moreover, in this embodiment, only a portion of the sidewall 338 of the second lumen 336 will include side portals 340, to create the necessary distance between the distal most side portal 340 and the outflow portal 332 of the first lumen 324.

Referring now to FIGS. 4-6, the fluid expelled from the system and into the patient may include native CSF (as shown in FIG. 4), a mixture of native CSF and a medicament (as shown in FIG. 5), a mixture of a synthetic CSF solution and/or a medicament (as shown in FIG. 6), or a combination of thereof.

As shown in FIG. 4, the pump 50, such as an infusion pump, is designed to receive fluid from an outside source and continuously deliver the same volume of cooled and/or pressurized fluid back to the patient via the first lumen 24 of the catheter 22 (such as the one shown in FIG. 2), maintaining a dynamic equilibrium in the patient's system over time. The rate of recirculation may be adjusted within a wide range, but is generally calculated to maintain the patient's own internal pressure and circulation rate. The pump 50 may have also have an aspiration mode.

The pump 50, located outside of the patient's body, also includes a cooling apparatus 52 and a pressurizing mechanism 54. A suitable cooling apparatus 52 and pressurizing mechanism 54 may be incorporated into the pump 50. As shown in FIG. 4, the pump 50 is generally connected to the first lumen 24 of the catheter 22. In one embodiment, the first lumen 24 may be connected to the pump 50 with a tubing 56 that extends between an output channel 58 of an output reservoir 60 in the pump 50 and the inflow portal 28 of the first lumen 24. By connecting the pump 50 directly to the first lumen 24, the system 20 remains closed and sterile for the duration of the patient's treatment. The output reservoir 60 may generally be configured to receive cooled and/or pressurized fluid (i.e. fluid).

Referring specifically to FIG. 4, native CSF may be drawn into the system 20 through the side portals 40 in the second lumen 36 of the catheter 22. The native CSF is then drawn through the outflow portal 44 of the second lumen 36 to the pump 50 where it is cooled and/or pressurized. In this embodiment, the second lumen 36 of the catheter 22 is connected to the pump 50 with a second tubing 62 that extends between an input channel 64 of an input reservoir 66 for receiving and containing, for example, the native CSF, and the outflow portal 44 of the second lumen 36.

Once in the pump 50, the native CSF is pressurized and cooled to a desired temperature and/or pressure, delivered to the output reservoir 60, and into a patient's intrathecal space via tubing 56 and the first lumen 24 of the catheter 22 as the native CSF continuously flows into the input reservoir 66 from the second lumen 36.

FIG. 5 shows a second embodiment of a system, system 120. As shown in FIG. 5, pump 150 may be used deliver a fluid to the patient's intrathecal space that includes a mixture of native CSF and a medicament. In the embodiment, the native CSF is withdrawn from the patient and mixed with a medicament, either outside or inside the input reservoir 66. As shown in FIG. 5, the medicament may be delivered to the input reservoir 66 via a second input channel 68, while the native CSF is delivered from the second lumen 36 through the input channel 64, as discussed above. In this embodiment, the mixture of the medicament and the native CSF is drawn into the pump 150 at a rate sufficient to keep the amount of fluid delivered to the intrathecal space surrounding the patient's spinal cord and brain constant.

It should be noted that generally, the addition of the medicament, such as a vasodilator, will not materially change the volume of native CSF being pumped from the input reservoir 66 to the output reservoir 60. If, for example, an antibiotic is being mixed with the native CSF, which substantially changes the volume of the fluid produced, an amount of native CSF can be withdrawn from the patient 1) before the system 120 is deployed within the patient or 2) after the system 120 has been deployed, but before the native CSF is mixed with the medicament.

Another embodiment of the system s shown in FIG. 6, the system 220. In this system 220, the native CSF withdrawn from the patient may be discarded to a chamber outside the patient's body, such as a medically approved waste container 70, via second tubing 62, and replaced with a synthetic CSF (medicated or un-medicated). The synthetic CSF may be housed in a third reservoir 72 (integral or separate from the pump 250) and delivered to the input reservoir 66 through the input channel 64 because the outflow portal 44 of the second lumen 36 is connected to the waste container 70. This alternative may be used in the situation where the patient is suffering from an infection or a subarachnoid hemorrhage.

Referring again to FIGS. 4-6, once delivered to the input reservoir 66, the native CSF, native CSF/medicament mixture, or the synthetic CSF is drawn through the cooling apparatus 52 where it is cooled to a specified temperature. The cooling apparatus 52 may be configured to cool the fluid from the input reservoir 66 to about 15° C. to about 37° C.

The cooling apparatus 52 may optionally include a temperature regulation system. The temperature regulation system may include, for example, a first thermostat 74 located within the second lumen 36 of the catheter 22 (as shown in FIG. 4), the input reservoir 66 of pump 150 (as shown in FIG. 5), or the third reservoir 72 (as shown in FIG. 6). The first thermostat 74 measures the temperature of the incoming fluid from the body or the third reservoir 72. A second thermostat 76 (as shown in FIGS. 4-6) measures the temperature of the outgoing fluid before it leaves via the output channel 58. The second thermostat 76 may be located at or around the output channel 58 of the pump.

The cooling apparatus 52 is located between the input reservoir 66 and the output reservoir 60 and may include a sealed cooling coil 82 containing a recirculated pressurized liquid refrigerant. In the embodiments shown and described, the pump and the cooling apparatus 52 are integral, but it is contemplated that they can be non-integral or separate components of the system.

Referring again to FIG. 4, After the fluid is cooled, it is pressurized in the pump 50 with the pressurizing mechanism 54, such as, for example, a piston driven pump. The pressurizing mechanism 54 and the pump 50 are integral, but it is contemplated that the they can he non-integral or separate components of a system. In one embodiment, the pressurizing mechanism 54 is used to impart pressure to or to increase the pressure of the fluid as it is delivered from the output reservoir 60 to the first lumen 24. In another embodiment, the pressurizing mechanism 54 imparts pressure to the fluid before it is delivered to the output reservoir 60. The pressurizing mechanism 54 may operate by increasing or decreasing the flow rate of the fluid from the input reservoir 66 to the output reservoir 60, or may impart pressure to the outflow of the fluid with any other known mechanism. In another embodiment, the pressurizing mechanism 54 may be used to impart pressure to the fluid before it is cooled by the cooling apparatus 52.

The pressure of the fluid may optionally be simultaneously monitored by separate or integrated sensors. It should be noted that the pressure sensors and the thermostats can be integrally formed. As shown in FIGS. 4-6, a first pressure sensor 78 may be disposed within the second lumen 36, at or around the side portals 40, to monitor the pressure of the native CSF as it leaves the patient's body. The pressure of the fluid may then be regulated within certain physiologic limits using the pressurizing mechanism 54, generally 5-200 mm Hg, although the pressure many be greater than 200 mm HG according to the desired effect and target of the fluid, i.e. the brain or spinal cord. A second pressure sensor 80 may be disposed at the output channel 58 of the pump or at the outflow portal 32 of the first lumen 24 to monitor the pressure of the fluid leaving the system. Any suitable pressure sensor, such as those available from the Codman Company, may be used to monitor the pressure within the patient's intrathecal space.

By pressurizing the fluid, one can ensure that the fluid will reach the intended target, a patient's intracranial compartment. Without sufficient pressure, the rate of dispersion of the fluid to the intracranial compartment will be insufficient to permit therapeutic cooling. Moreover, if the fluid is not pressurized, the temperature of the fluid may increase to an ineffective temperature before penetrating the intracranial compartment.

The only way to cure this defect without increasing the pressure of the fluid would be to cool the fluid to a level that may be injurious to the spinal cord and its elements, or else to a level that would alter the physical properties of the fluid by viscosity and crystallization. Even then, penetration of the intracranial compartment may not occur at all. It should be noted that augmentation of the pressure of the fluid even beyond the usual physiologic range is not necessarily harmful, and often well-tolerated by the inherent natural capacitance of the intrathecal space. It is contemplated that the fluid may be pressurized up to 400 mmHg.

As shown in FIG. 4, after cooled and pressurized, the fluid is passed through the output channel 58 of the pump 50 to the first lumen 24 of the catheter 22, where it is expelled through an outflow portal 32 in the distal end 30 of the first lumen 24 into the patient's body.

The second lumen 36 is not pressurized, but passive. The intake of native CSF is generally dependent upon the hydrostatic pressure in the native CSF, and augmented by gravitational hydrostatic pressure. At a given native CSF fluid pressure, the side portals 40 along the sidewall 38 transmit native CSF passively to the second lumen 36, and a dynamic equilibrium of fluid input and output to the intrathecal space will be established. At a given native CSF pressure, the design of the catheter 22 causes the native CSF to enter the side portals 40, which are at a lower pressure than the surrounding intrathecal space. The surrounding native CSF will not enter the first lumen 24 because the fluid in the first lumen 24 is pressurized by the pump 50. The result is that pressurized fluid exits the catheter 22 centrally and the surrounding native CSF enters the catheter 22 peripherally. A dynamic equilibrium is thus established and maintained.

Such an equilibrium may be achieved at various levels of CSF pressurization, so the speed of irrigation of the intrathecal space will vary according to the selected pressure range. Also, that the volume of the intrathecal space being irrigated is variable within a physiologic range, because of inherent distensibility of the enveloping meningeal membranes.

In addition, the rate of flow within the second lumen 36 will be affected by gravitational hydrostatic pressure, such that positioning the proximal end 42 of the second lumen 36 of the catheter 22 below the lumbar access point into the patient will result in more rapid egress of native CSF from the patient.

By modifying the pressure and physical properties of the fluid that is circulated into the patient, the system 20 facilitates dispersion of a fluid to the patient depending on the selected modality (filtration, irrigation, cooling, antisepsis, or blood flow augmentation). The different modalities are utilized according to the clinical problem, and imparted by changing the physical properties of the fluid.

For example, as shown in FIG. 6, for general neuroprotection, the fluid that is delivered to the input reservoir 66 may include a synthetic CSF that is cooled. To treat a patient suffering from an infection, an antibiotic may added to the fluid before or after it is cooled. To treat a stoke patient, certain compounds, such as nitric oxide donors, that are effective to impart vasodilation, may be added to the synthetic CSF (FIG. 6) or to the native CSF (FIG. 5) before it is cooled.

Moreover, to clear severe CNS infection or to remove blood in the patient's intrathecal space after an aneurysm rupture, the system 220 may be used to deliver synthetic CSF, cooled or not, to a patient's subarachnoid/intrathecal space at relatively high pressure. according the system 220 shown in FIG. 6. The pressures selected for these modalities would assure optimal delivery of fluid, and a dynamic equilibrium of fluid exchange.

In another embodiment, the system may be used to treat seizures of the brain, manifested by abnormal spread of electrical activity among neurons of the cortex. Delivery of fluid to the CNS by way of the intrathecal space, as described in any of the embodiments, would be advantageous in terminating seizures and the condition of status epilepticus.

Prophetic Example

A patient presents to the hospital with signs and symptoms of a stroke in evolution. A CT scan of the brain is performed to demonstrate that there is no brain hemorrhage. The patient's neurological signs demonstrate aphasia and paralysis of the right arm, indicating a stroke in evolution involving the left cerebral hemisphere in the distribution of the middle cerebral artery. The patient is known to have had recent surgery; therefore intravascular thrombolytic agents cannot be used. Instead, the patient undergoes catheterization of his lumbar thecal sac, permitting the administration of a stroke medication that contains properties of site-specific vasodilation effective from the adventitial side of a blood vessel, anti-platelet aggregation, and anti-microvascular sludging. The medication is mixed with the patient's own or a synthetic CSF and delivered using the system, as described above with regard to FIGS. 5-6.

The patient's CSF pressure measurement is immediately obtained after insertion of the catheter, either by measuring the height of the column of CSF against gravity or by using a pressure sensor attached to, or integrated within, the second lumen of the catheter. In this case the initial pressure is normal (e.g., 15 mm Hg). Because it is desired to reach the intracranial compartment with the medicated fluid, it is necessary to pressurize the fluid to mm Hg (upper limit of normal pressure) in order to optimize the delivery of the medication in the to the brain of the patient. Alternatively, a lower pressurization may be utilized, in combination with tilting the patient into Trendelenburg position, with or without additionally employing a fluid that is more dense than the native CSF. In either case, maintaining a cerebral perfusion pressure in the proper range for optimal cerebral blood perfusion (60-80 mm Hg) provides a guideline for pressurization (see below: cerebral perfusion pressure CPP=mean arterial blood pressure MABP minus intracranial (CSF) pressure (ICP)).

Because the fluid contains no thrombolytic activity, its use is not contraindicated in this patient, and because it is not a thrombolytic, there is no time limitation for its administration to the patient. Because the fluid is therapeutically cooled to a desired temperature, e.g., 33° C., it possesses the additional intrinsic property of localized neuronal protection. The delivery of the medication in the fluid is localized within the CNS and, therefore, total body cooling is not required.

In addition, the necessity of general anesthesia or sedation may be obviated, and the medication, via the fluid, can be given to the awake patient, affording the advantage of being able to follow his neurological examination at periodic intervals to measure the effectiveness of treatment. Because its administration is confined to the patient's intrathecal space, the fluid is in direct and immediate contact with, and protection of the central nervous tissue at risk. Moreover, because the fluid may consist of a synthetic CSF with a density different from native CSF, the distribution of the fluid can be controlled by tilting the patient, and it may be delivered to the brain from a lumbar intrathecal access site.

In this example, the effects of vasodilation, anti-platelet aggregation, and anti-microvascular sludging are mediated by a mechanism (cyclic GMP activated by nitric oxide) that traverses the blood vessel wall from the intrathecal space, and these actions are effected by the medication when it is administered in the fluid. Therefore, the neuroprotective nature of the fluid is augmented by local hypothermia of the treated tissue and the fluid can still be protective for this patient even if infarction has already occurred.

In this hypothetical situation, a core of infarction exists, surrounded by a penumbra of damaged, but not yet infarcted, nervous tissue. Hypothermic protection of this penumbra will therefore assist in limiting the damage caused by the initial stroke and its attendant edema, among other mechanisms of secondary brain and spinal cord injury.

Prophetic Example

Spinal Cord Trauma

A patient involved in a motor vehicle accident presents to the Emergency Department of a hospital with acute nonpenetrating trauma to the spinal cord. Neurological examination demonstrates complete paraplegia. Hypothermia protection is considered, but is impractical because it would require intubation, pharmacologic paralysis and induced coma; yet the patient is awake and alert because there is no brain injury.

Instead, the patient undergoes catheterization of the thecal sac of the subarachnoid space, using the system shown in FIG. 6, and receives a fluid, which provides localized hypothermia. Because the patient has had traumatic spine injury, blood exists within the CSF of the spinal cord. As described above, the system may be used to remove the native CSF and replace it with synthetic CSF. The removal of the inflammatory influence of this blood in contact with damaged CNS tissue, in conjunction with the hypothermic protection of damaged neurons of the CNS, optimizes recovery from this neurological injury. In this case, minimal pressurization is required to deliver the fluid to the site of injury, since the latter is very close to the lumbar thecal access point.

Prophetic Example

Cerebrovascular Accident with Altered Mental Status

A patient presents to the Emergency Department of a hospital with painless weakness of the right side of his body and speech dysfunction. Neurological examination demonstrates right hemiplegia and aphasia. CT scan of the brain demonstrates low attenuation changes of the left cerebral hemisphere in the distribution of the middle cerebral artery, with cerebral edema: he also exhibits confusion and lethargy. The history indicates that the patient had weakness before going to bed the previous evening. Because he is beyond the usual time window for administration of a thrombolytic agent, therapeutic options arc limited. Endovascular surgical options are also eliminated by the relatively late presentation.

Neuroprotection is now a central feature of available therapeutic options. Because the patient has altered mental status and is demonstrating neurological deterioration with evidence of early cerebral edema on the CT scan, prudent management is intubation and transfer to Intensive Care Unit, with institution of cerebral protection by any of several available methods, including pentobarbital coma and hypothermia. Disadvantages of pentobarbital coma include infection, disturbance of gut motility with resultant insufficient nutrition, cardiovascular collapse, and hypotension. Disadvantages of systemic hypothermia include pulmonary infection, overwhelming sepsis and death, and bleeding from coagulation abnormalities.

It is decided that the patient may experience the least risk with site-specific, organ system-specific hypothermia delivered to the CNS. The system as described with regard to FIGS. 4-6 may be used to deliver a fluid. The fluid may include native or synthetic CSF. In this situation the patient's CSF is cooled by convection as the fluid is pumped into the space surrounding the damaged brain 14 tissue.

Alternatively, the system ay be used to deliver a hyperbaric fluid, including synthetic CSF, which reaches the intracranial space rapidly through simple tilting of the patient into Trendelenburg position (head down). Alternatively, the system may be used to deliver a hypobaric fluid, including synthetic CSF, which reaches the intracranial space rapidly through simple tilting of the patient into reverse-Trendelenburg position (head up).

In this example, pressurization of fluid is preceded by measurement of patient's CSF pressure upon insertion of the catheter by the methods described above. Although cerebral edema is present, intracranial pressure elevation has not yet occurred and the decision to pressurize is made. If, on the other hand, it is believed that intracranial pressure is already elevated (>20 mm Hg), it may be prudent to make use of hyperbaric medication with Trendelenburg tilting in lieu of pressurization.

In another example, hypothermic neuroprotection may be effected by using the system, wherein the catheter is a ventricular catheter that is installed into the patient through a ventricular access point, as opposed to a lumbar access point. In the case of the comatose or obtunded patient, this option may be easily substituted, whereas with the fully awake stroke patient, the lumbar route of administration may be more preferred. If this option is utilized, CSF may be directly withdrawn from the patient's head and a low pressure may rapidly be therapeutically established for the express purpose of proceeding with medication-induced pressurization.

Prophetic Example

Cerebrovascular Accident without Altered Mental Status

A patient presents to the emergency department of a hospital with acute stroke. He has arrived at the hospital approximately 4 hours after the stroke: therefore, he is ruled out as a candidate for intravenous tPA, and the hospital does not have availability of a neurointerventional specialist for consideration of intraarterial thrombolysis. Examination reveals him to be awake and alert, with paralysis of the left side of his body. CT perfusion scan demonstrates a large area of the right cerebral hemisphere with infarction in the distribution of the right middle cerebral artery, and also a large area of brain tissue with diffusion/perfusion mismatch, indicating that a larger area of brain tissue is at risk to go on to cerebral infarction.

Therapeutic options are now limited to optimization of collateral circulation of the brain, and neuroprotection. From the effects of cerebral edema and inflammatory brain reaction, the patient is at risk for neurological deterioration and more extensive infarction within the next several days. Because he is alert, the surgical procedure of decompressive hemicraniectomy is not under immediate consideration. For the same reason, systemic hypothermia with intubation and pharmacologic paralysis are not immediate considerations. The patient would benefit ideally from a localized form of neuroprotection that does not involve cooling of the entire body that is provided by the proposed invention.

The patient may have local anesthesia to the skin of the lumbar spine for the purpose of installing the system, described above with regard to FIGS. 4-6, without the need for general anesthesia. CSF pressure measurement is made upon insertion of the catheter and found to be normal (e.g., 10 mm Hg). Thereafter, the system is used to withdraw native CSF, cool it, and deliver the fluid to the patient's brain at a pressure of approximately 15-20 mm Hg, with or without tilting, The patient in this example may also benefit from the lumbar intrathecal administration of a medicated fluid for stroke, as shown in FIGS. 5-6, such as the solution that is the subject of currently pending U.S. application Ser. No. 12/412, 011. filed on Mar. 26, 2009. This fluid provides the optimization of available collateral blood vessels, increasing regional cerebral blood flow and local cerebral oxygen tension and may be delivered in cooled form to provide additional neuroprotection via hypothermia.

Prophetic Example

Brain Trauma, CHT

A patient presents to the emergency department of a hospital, having sustained closed head trauma with subsequent brain injury. The patient's CT scan demonstrates frontal and temporal contusions and generalized brain edema. Intracranial hypertension is diagnosed based on review of CT scan and clinical condition of the patient. In this case, the patient suffers from raised intracranial pressure consequent to brain contusion and edema. This condition can be expected to be aggravated over the next 3-5 days, as cerebral edema and inflammatory brain reaction evolve. The cause of neurological deterioration and death in such cases is frequently this type of secondary brain injury which reliably follows the trauma. A treatment to diminish and mitigate this reaction would be valuable, although there are disadvantages to the use of whole-body hypothermia, such as pulmonary infection and bleeding abnormalities, which in themselves could worsen the bleeding contusions in the brain, and other injuries.

The system and its methods of use are therefore selected and a cranial/ventricular or lumbar intrathecal access to the CSF is established. In such a case, the use of ventricular access simultaneously provides excellent control of intracranial pressure, which is expected to be elevated because of the nature of the injury, and avoids any potential problem of craniospinal pressure dissociation, and is therefore more desirable than lumbar intrathecal access. The CNS of the patient is selectively cooled to a desired temperature, between 15 and 37 degrees Celsius, as the patient's CSF is recirculated by the pump, as shown in FIG. 4. In an alternative method, synthetic CSF is used to substitute a portion or the entirety of the native CSF (FIGS. 5-6).

In yet another alternative embodiment, the synthetic CSF is hyperbaric and flows rapidly cephalad as the patient is moved into Trendelenburg position, more rapidly reaching the target tissue of the brain and bathing it. The treatment is administered for a time period corresponding to the most severe phase of the illness, e.g., 3-5 days. Since systemic hypothermia is obviated, bleeding complications and infectious complications related to that treatment are avoided, while preserving its neuroprotective benefits.

Prophetic Example

Cerebral Hypoperfusion

A patient suffering from severe cerebral ischemia from hypoperfusion secondary to intracranial arterial stenosis is under observation in the intensive care unit. The patient has no neurological deficit, but develops right hemiparesis and aphasia when his mean arterial blood pressure is permitted to fall below 100 mm Hg. Therefore, he is maintained on pressor agents (such as Neosynephrine) and intravascular volume expansion with colloid and crystalloid in order to prevent a fall in blood pressure. His collateral circulation will mature sufficiently within the next several days, to the point that he will no longer be dependent on this management to preserve his brain function. His cardiac function, however, has become marginal within the last 12 hours, and he is exhibiting signs of congestive heart failure. Because of this it has become progressively more difficult to maintain adequate blood pressure. CT perfusion scan is done, demonstrating no infarction but rather a diffusion/perfusion mismatch that identifies a substantial portion of the left cerebral hemisphere as being at risk for stroke.

Under these circumstances, therapeutic maneuvers to confer neuroprotection are desirable. Hypothermia will slow the metabolism of the target tissue, rendering it less vulnerable to ischemic injury for the time period necessary for the patient to optimize his collateral circulation. In administering localized, site-specific hypothermia using the system as shown in FIGS. 4-6, systemic effects and disadvantages of whole-body hypothermia are avoided. Because no injury to brain tissue has yet occurred, CSF pressure is normal and there is no contraindication to pressurization of the CSF by lumbar intrathecal route. In this case it is desirable to pressurize the fluid to 15-20 mm Hg, with or without tilting, in order to enhance delivery of the fluid to the intracranial compartment. MABP is therefore maintained at 85-90 mm Hg.

In an alternative embodiment, the fluid has antiplatelet, anti-microvascular sludging, and vasodilator properties, all such properties contributing to improved rheology and volume of collateral circulation.

Prophetic Example

Cerebral Vasospasm

A patient presents to the hospital with ruptured cerebral aneurysm and subarachnoid hemorrhage (SAH). The clinical grade is moderate (the patient is awake without focal deficit), but the radiographic grade is consistent with a voluminous SAH and therefore risk of cerebral vasospasm. His aneurysm is treated by neurosurgical operation within 24 hours, and his recovery in ICU is unremarkable for 6 days. On the 7th day, however, he develops obtundation and hemiparesis. Transcranial Doppler reveals cerebral vasospasm in the right middle cerebral artery, the location of the ruptured and now clipped aneurysm. This is confirmed by CT angiography, and CT perfusion shows a diffusion/perfusion mismatch in a substantial region of the right hemisphere served by the middle cerebral artery, Symptomatic cerebral vasospasm is therefore established, and substantial cerebral territory at risk of infarction is defined. Although cerebral balloon angioplasty may be used in this situation, it is limited by the requirement for experienced neurointerventional personnel and equipment, as well as by the anatomical distribution of the vasoconstriction (angioplasty can only be performed in the proximal vasculature, whereas the effects of vasospasm are wide-reaching). Intravascular volume expansion and induced hypertension have limited power to alleviate the condition, and may not be usable at all in elderly patients or in patients prone to congestive heart failure or volume overload.

Under these conditions, it is advantageous to confer hypothermic protection upon the brain at risk, and to do so in a manner that does not invite systemic complications such as pulmonary infection and bleeding in this patient with recent SAH. Thus, the patient is treated with lumbar thecal catheterization using the system shown in FIGS. 4-6. Selective hypothermic brain protection is administered via the fluid. Pressurization of the fluid is implemented to enhance intracranial delivery.

Because induced hypertension is being used in this patient for the treatment of vasospasm, higher fluid pressures (e.g., 20-30 mm Hg) may be utilized, as long as cerebral perfusion pressure (CPP) (mean arterial blood pressure (MABP) minus intracranial ((CSF)) pressure) is maintained. Acceptable CPP is in the range of 60-80 mm Hg, and is often driven deliberately higher by induced hypertension in the vasospasm or stroke patient. Thus, MABP is driven to 100 mm Hg in the present patient, by use of pressors and hypervolemia, and CSF pressure of 30 mm Hg is established, yielding a CPP of around 70 mm Hg, ideal for optimal vascular perfusion.

In an alternative treatment paradigm, the fluid is synthetic CSF and contains agents conferring properties of vasodilation, antiplatelet, and anti-microvascular sludging. The fluid may also be hypobaric or hyperbaric for more rapid or accurate delivery to the intracranial intrathecal space.

Prophetic Example

Leptomeningeal Infection

A patient is admitted to the intensive care unit of the hospital with high fever and delirium. Examination reveals clouded sensorium, neck stiffness with positive clinical signs of meningitis (Kernig's and Brudzinski's signs). The patient's body temperature is 39.5° C. The patient undergoes CT scan of the brain which reveals no evidence of hemorrhage or mass lesion. A lumbar puncture is performed and reveals bacteria in the CSF, with hypoglycorrhachia and elevated neutrophil count. The diagnosis of bacterial meningitis is established and appropriate antibiotics are begun.

Under these circumstances, the physician uses the system as disclosed in FIG. 6, to administer, via the lumbar access point, a fluid to the patient's intrathecal space to flush out the bacteria laden native CSF and replace it with a synthetic fluid. Intracranial (CSF) pressure is at the upper limit of normal (20 mm Hg), and pressurization of the fluid at or slightly above this level is established. MABP is maintained at 90-110 mm Hg in order to assure adequate brain tissue vascular perfusion. The fluid is used to irrigate the intrathecal space.

In another example, the fluid is cooled to a predetermined temperature, affording a means to selectively cool CNS elements directly in contact with it, thereby providing localized neuroprotection against harmful effects of inflammation and hyperthermia.

In yet another example, the fluid is hyperbaric or hypobaric for more rapid and accurate delivery to the intracranial intrathecal space. In this example, somewhat lower pressurization level (e.g., 15 mm Hg) is required to achieve the target (brain) tissue. The treatment is delivered in this manner for several days or longer, as long as the threat to central nervous tissue persists. The treatment may also be protective against seizure disorder.

Prophetic Example

Subarachnoid Hemorrhage

A patient presents to the hospital with high-grade aneurysmal subarachnoid hemorrhage. The abundance of blood in the intrathecal space consequent to the hemorrhage, besides immediately threatening the patient's life through abruptly increased intracranial pressure, creates other hazards consequent to inflammatory brain response (cerebral edema) and delayed chronic cerebral vasoconstriction (vasospasm). These inflammatory responses are associated with the blood itself in the intrathecal space. Therefore, the blood must be either partially or entirety removed from the intrathecal space to mitigate or prevent complications.

Therefore, the system as shown in FIG. 6, is instituted for the purpose of therapeutic irrigation of the patient's CSF, either by delivering a fluid that includes a synthetic CSF or by cleansing native CSF with a filtration system, as described above.

In another example, the fluid is cooled to a predetermined temperature in the range of 15 to 37° C. for purposes of neuroprotection.

Prophetic Example

Status Epilepticus

A patient is admitted to the hospital with continuous grand mal seizures. The patient s unable to return to a wakeful state before the next seizure occurs, thereby meeting the criterion for status epilepticus and neurological emergency. A prescribed medical regimen for the emergency treatment of this dangerous condition exists, but is not always successful, whereupon general anesthesia is instituted.

Administration of cold saline to the seizing brain may immediately halt seizure, therefore, the therapeutic cooling of the CSF, in direct and universal contact with the brain 14 and spine, may have a similar beneficial effect in arresting seizures. Adequate pressurization of the fluid (e.g., 15-20 mm Hg) is necessary to reach the target organ in this case, and MABP is maintained at a level adequate to assure optimal CPP.

In this case, therefore, the failure of the medical regimen to arrest the seizures results in the implementation of the system as shown in FIGS. 4-6, obviating the necessity for general anesthesia. Alternatively, if general anesthesia had been required for circumstantial reasons to arrest the seizures, the implementation of the system with a fluid would make it possible to remove general anesthesia from the patient.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the present application has been illustrated by the description of embodiments thereof, and while the embodiments have been described in considerable detail, it is not the intention of the applicant to restrict or in any way limit the scope of the appended claims to such detail. Therefore, the application, in its broader aspects, is not limited to the specific details, the representative apparatus and method, and illustrative examples shown and described. Accordingly, departures may be made from such details without departing from the spirit or scope of the applicant's general inventive concept.

The invention claimed is:

1. A system for treating or preventing damage to a patient's central nervous system, the system comprising:
   a catheter comprising at least a first lumen and a second lumen,
   wherein the first lumen comprises a proximal end having at least one inflow portal and a distal end having at least one outflow portal, and
   wherein the second lumen comprises a proximal end and a distal end and a sidewall extending between the proximal end and the distal end, the sidewall having at least one side portal providing fluid communication between an outer surface of the sidewall and an inner surface of the sidewall, and the proximal end of the second lumen having at least one outflow portal, and a first pressure sensor at or around at least one of the side portals; and
   a single pump comprising at least one input channel, an input reservoir in fluid communication with said at least one input channel, a cooling apparatus configured to remove heat from a fluid, a pressurizing mechanism configured to augment pressure of the fluid beyond the physiologic range so that the pressurized fluid is intended to move from the intrathecal space of the spine to the intracranial compartment of brain, an output reservoir, and an output channel comprising a second pressure sensor; and wherein the single pump is configured to cool a fluid, increase the pressure of the fluid to a pressure that is greater than a pressure of the patient's native cerebral spinal fluid to create a pressurized fluid, and deliver the pressurized fluid to the body of the patient.

2. The system of claim 1, wherein the first lumen of the catheter is substantially concentrically disposed within the second lumen of the catheter.

3. The system of claim 1, wherein the first lumen is longitudinally adjacent to the second lumen, and wherein the first lumen and the second lumen are separated by a partitioning wall.

4. The system of claim 1, wherein the output channel is configured to be connected to the inflow portal of the first lumen.

5. The system of claim 4, wherein the outflow portal of the second lumen is configured to be connected to the input channel of the input reservoir.

6. The system of claim 5, wherein the pump further comprises a second input channel in fluid communication with the input reservoir.

7. The system of claim 4, wherein the outflow portal of the second lumen is configured to be connected to a waste container, and wherein the input channel of the input reservoir is configured to be in fluid communication with a third reservoir.

8. The system of claim 1, wherein the pressurized fluid has a pressure from at least about 5 mmHg to about 400 mmHg before it is delivered to the body of the patient.

9. The system of claim 1, wherein the second lumen may have plurality of side portals.

10. The system of claims 1 wherein the first pressure sensor monitors the pressure of the cerebrospinal fluid leaving the patient's body and the second pressure sensor monitors an intended and desired increase in the pressure of cooled cerebrospinal fluid leaving the pump and entering the patient's body.

11. A method for treating or preventing damage to the central nervous system, comprising providing the system of claim 1;
inserting the catheter into the patient so that the at least one side portal of the second lumen of the catheter is disposed within an intrathecal space of the patient;
withdrawing a portion of native cerebral spinal fluid from the patient through the at least one side portal;
delivering the portion of native cerebral spinal fluid to the input reservoir of the pump;
cooling the portion of native cerebral spinal fluid;
pressurizing the portion of the native cerebral spinal fluid; and
re-introducing the portion of the native cerebral spinal fluid to the intrathecal space of the patient through the first lumen of the catheter at a pressure equal to or greater than 5 mmHg.

12. The method of claim 11, wherein the pump further comprises a second input channel configured to deliver a medicament to the input reservoir, wherein the medicament and the portion of native cerebral spinal fluid are combined to form a mixture in the input reservoir before mixture is cooled and pressurized.

13. A method for treating or preventing damage to the central nervous system, comprising providing the system of claim 1;
inserting the catheter into a patient so that the at least one side portal of the second lumen of the catheter is disposed within an intrathecal space of the patient;
withdrawing a portion of native cerebral spinal fluid from the patient through the at least one side portal;
discarding the portion of native cerebral spinal fluid;
delivering a fluid to the input reservoir of the pump;
cooling the fluid;
pressurizing the fluid; and
introducing the fluid to the intrathecal space of the patient through the first lumen of the catheter at a pressure equal to or greater than 5 mmHg.

14. The method of claim 13, wherein the fluid comprises a synthetic cerebral spinal fluid, a medicament, or a combination thereof.

15. A system for treating or preventing damage to a patient's central nervous system, the system comprising:
a catheter comprising at least a first lumen and a second lumen,
wherein the first lumen comprises a proximal end having at least one inflow portal and a distal end having at least one outflow portal, wherein the outflow portal is configured to deliver fluid into a patient's intrathecal space below the lumbar region of a patient's body;
wherein the second lumen comprises a proximal end and a distal end and a sidewall extending between the proximal end and the distal end, the sidewall having at least one side portal providing fluid communication between an outer surface of the sidewall and an inner surface of the sidewall, and the proximal end of the second lumen having at least one outflow portal, and a first pressure sensor;
a pump comprising at least one input channel, an input reservoir in fluid communication with said at least one input channel, a cooling apparatus configured to remove heat from a fluid, a pressurizing mechanism configured to augment pressure of the fluid beyond a physiological range so that the pressurized fluid is intended to move from the intrathecal space of the spine to the intracranial compartment of brain, an output reservoir, and an output channel with a second pressure sensor; and
wherein the pump is configured to cool a fluid, increase the pressure of the fluid to a pressure that is greater than a pressure of the patient's native cerebral spinal fluid to create a pressurized fluid, and deliver the pressurized fluid to the intrathecal space below the lumbar region of the patient's body.

16. The system of claim 15 wherein the first pressure sensor monitors the pressure of the cerebrospinal fluid leaving the patient's body and the second pressure sensor monitors an intended and desired increase in the pressure of cooled cerebrospinal fluid leaving the pump and entering the patient's body.

* * * * *